(12) United States Patent
Nappa et al.

(10) Patent No.: US 8,907,145 B2
(45) Date of Patent: Dec. 9, 2014

(54) AEROSOL PROPELLANTS COMPRISING UNSATURATED FLUOROCARBONS

(75) Inventors: Mario Joseph Nappa, Newark, DE (US); Joseph Anthony Creazzo, Wilmington, DE (US); Allen Capron Sievert, Elkton, MD (US); Ekaterina N. Swearingen, Wilmington, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 13/594,007

(22) Filed: Aug. 24, 2012

(65) Prior Publication Data

US 2012/0318828 A1 Dec. 20, 2012

Related U.S. Application Data

(62) Division of application No. 11/590,344, filed on Oct. 30, 2006, now abandoned.

(60) Provisional application No. 60/732,292, filed on Nov. 1, 2005.

(51) Int. Cl.
| | | |
|---|---|---|
| C07C 17/00 | (2006.01) | |
| C07C 19/08 | (2006.01) | |
| C07C 21/18 | (2006.01) | |
| C07C 23/00 | (2006.01) | |
| C07C 25/13 | (2006.01) | |
| C09K 3/30 | (2006.01) | |
| A61K 9/12 | (2006.01) | |

(52) U.S. Cl.
CPC .. *C09K 3/30* (2013.01); *A61K 9/124* (2013.01)
USPC ........................................................ 570/126

(58) Field of Classification Search
CPC ....................................................... C09K 3/30
See application file for complete search history.

(56) References Cited

U.S. PATENT DOCUMENTS

| | | | |
|---|---|---|---|
| 3,085,918 A | 4/1963 | Sherliker | |
| 3,723,318 A | 3/1973 | Butler | |
| 3,884,828 A | 5/1975 | Butler | |
| 4,085,073 A | 4/1978 | Suh et al. | |
| 4,394,491 A | 7/1983 | Hoffman | |
| 4,613,708 A | 9/1986 | Riess et al. | |
| 4,704,410 A | 11/1987 | Booth et al. | |
| 4,704,411 A | 11/1987 | Gansow et al. | |
| 5,037,572 A | 8/1991 | Merchant | |
| 5,087,777 A * | 2/1992 | Li et al. ......................... | 570/136 |
| 5,164,419 A | 11/1992 | Bartlett et al. | |
| 5,204,159 A | 4/1993 | Tan | |
| 5,332,761 A | 7/1994 | Paquet et al. | |
| 5,463,150 A | 10/1995 | Lui et al. | |
| 5,578,137 A | 11/1996 | Shealy | |
| 5,900,185 A | 5/1999 | Tapscott | |
| 5,908,822 A | 6/1999 | Dishart | |
| 5,977,271 A | 11/1999 | McKay et al. | |
| 6,071,580 A | 6/2000 | Bland et al. | |
| 6,590,005 B2 | 7/2003 | Singh et al. | |
| 6,610,250 B1 | 8/2003 | Tuma | |
| 6,703,431 B2 | 3/2004 | Dietzen et al. | |
| 6,787,580 B2 | 9/2004 | Chonde et al. | |
| 2004/0119047 A1 | 6/2004 | Singh et al. | |
| 2004/0256594 A1 | 12/2004 | Singh et al. | |
| 2005/0233934 A1 | 10/2005 | Singh et al. | |
| 2007/0077488 A1 | 4/2007 | Chen et al. | |
| 2007/0096051 A1 | 5/2007 | Nappa et al. | |
| 2007/0098646 A1 | 5/2007 | Nappa et al. | |
| 2007/0100009 A1 | 5/2007 | Creazzo et al. | |
| 2007/0100010 A1 | 5/2007 | Creazzo et al. | |
| 2007/0100011 A1 | 5/2007 | Creazzo et al. | |
| 2007/0102021 A1 | 5/2007 | Nappa et al. | |
| 2007/0105738 A1 | 5/2007 | Nappa et al. | |
| 2007/0108403 A1 | 5/2007 | Sievert et al. | |
| 2007/0203046 A1 | 8/2007 | Minor et al. | |
| 2008/0269532 A1 | 10/2008 | Swearingen | |

FOREIGN PATENT DOCUMENTS

| | | |
|---|---|---|
| DE | 2534315 A1 | 2/1976 |
| EP | 0558763 A1 | 8/1993 |
| EP | 0398147 B1 | 9/1994 |
| EP | 0731162 | 11/1996 |
| EP | 0350316 B1 | 2/1997 |
| GB | 950876 A | 2/1964 |
| JP | 05179043 A | 7/1993 |
| WO | 9423008 | 10/1994 |
| WO | 2004037913 A2 | 5/2004 |
| WO | 2005099718 A1 | 10/2005 |
| WO | 2006101882 A2 | 9/2006 |
| WO | 2008057513 A1 | 5/2008 |
| WO | 2008134061 A2 | 11/2008 |
| WO | 2008154612 A1 | 12/2008 |
| WO | 2009014965 A1 | 1/2009 |
| WO | 2009014966 A1 | 1/2009 |
| WO | 2009032983 A1 | 3/2009 |
| WO | 2009073487 A1 | 6/2009 |
| WO | 2009085857 A2 | 7/2009 |

OTHER PUBLICATIONS

U.S. Appl. No. 11/589,588, filed Oct. 30, 2006, Inventors Sievert et al.
U.S. Appl. No. 60/732,396, filed Nov. 1, 2005—U.S. Appl. No. 11/590,543, filed Oct. 31, 2006, Inventors Nappa et al.
U.S. Appl. No. 60/732,771, filed Nov. 1, 2005—U.S. Appl. No. 11/591,650, filed Nov. 1, 2006, Inventors Nappa et al.
U.S. Appl. No. 60/732,909, filed Nov. 1, 2005—U.S. Appl. No. 11/591,350, filed Nov. 1, 2006, Inventors Creazzo et al.
Jeanneaux et al., Journal of Fluorine Chemistry, vol. 4 (1974), pp. 261-270 (Summary in English.
"The Scientific Assessment of Ozone Depletion" (2002), Report of the World Meteorological Association's Global Ozone Research and Monitoring Project http://www.wmo.ch/pages/prog/arep/gaw/ozone_2002/ozone_2002.html.
PCT International Search Report for International Application No. PCT/US2006/042632 dated Apr. 4, 2007.

(Continued)

*Primary Examiner* — Clinton Brooks

(57) ABSTRACT

Disclosed herein are propellants comprising fluorocarbons and/or hydrofluorocarbons. Also disclosed are sprayable compositions comprising the propellants.

4 Claims, No Drawings

(56) References Cited

OTHER PUBLICATIONS

Doherty et al, Conceptual Design of Distillation Systems, McGraw-Hill (New York), 2001, 185-186, 351-359).

"Phase Equilibrium in Process Design", Wiley-Interscience Publisher, 1970, written by Harold R. Null, on pp. 124 to 126.

"The Properties of Gases and Liquids," 4th edition, published by McGraw Hill, written by Reid, Prausnitz and Poling, on pp. 241 to 387, 2000.

"Phase Equilibria in Chemical Engineering," published by Butterworth Publishers, 1985, written by Stanley M. Walas, pp. 165 to 244.

Boden et. al., Chapter 4, Polyurethane Handbook, Edited by G. Oertel, Hanser Publishers, NY 1985.

Grunbauer et. al., "Fine Celled CFC-Free Rigid Roam—New Machinery With Low Boiling Blowing Agents", Published in Polyurethanes 92 From the Proceeding of the SPI 34th Annual Technical/Marketing Conference, Oct. 21-24, 1992, New Orleans, Louisiana.

Taverna et. al., "Soluble or Insoluble Alternative Blowing Agents? processing technologies for Both Alternatives, Presented by Equipment Manufacturer", Published in Polyurethanes World Congress 1991 From the Proceedings of the SPI/SOPA Sep. 24-26, 1991, Acropolis, Nice, France.

Santini G. et. al., "The Reaction of Perfluoroalkylcopper Compounds With 1-Bromo-Perfluoroalkyethylenes", Tetrahedron, Vol. 29, 1973, p. 2411-2414, XP002427778, Table 3; Compound 2A, 2B.

Devallezbernard et. al., "Solubility of Respiratory Gases in the 1, 2-Bis(F-Alkyl) Ethenes", Journal De Chimie Physique, Societe De Chimie Physique, Paris, France, vol. 85, No. 10, 1988, p. 947-952, XP008077143.

Gao et al., "Dip-Coating of Ultra Think Liquid Lubricant and its Control for Thin-Film Magnetic Hard Disks", IEEE Transactions on Magnetics, vol. 31, No. 6, 1995, p. 2982-2984.

Le Blanc M et. al., "A Strategy for the Synthesis of Pure, Inert Perfluoroalkylated Derivatives Designed for Flood Substitution", Oxygen Carrying C9olloidal Blood Substitues, Iinternational Symposium Perfluorochem Blood Substitutes, 1982, pp. 43-49, XP008077176.

Skochdopole, R. E. et. al., "Polystyrene Foams", Encyclopedia of Polymer Science, vol. 16 (1989), pp. 193-206.

Pedler A. E. et. al., "The Synthesis and Dehydroflurination of Some Polyfluoroalkanes", J. Fluorine Chem., vol. 1 No. 3, 1972, p. 337-345, XP002427764.

\* cited by examiner

AEROSOL PROPELLANTS COMPRISING UNSATURATED FLUOROCARBONS

CROSS REFERENCE TO RELATED APPLICATION(S)

This application claims the benefit of priority to U.S. application Ser. No. 11/590,344 filed Oct. 30, 2006, and claims the benefit of priority to U.S. Provisional Application No. 60/732,292, the complete disclosure of which is incorporated herein by reference.

FIELD OF THE INVENTION

Disclosed herein are aerosol propellant compositions comprising unsaturated fluorocarbons or unsaturated hydrofluorocarbons. Also disclosed is the use of these compositions in preparing aerosol products.

BACKGROUND OF THE INVENTION

In the early 1970s, concern began to be expressed that the stratospheric ozone layer (which provides protection against penetration of the Earth's atmosphere by ultraviolet radiation) was being depleted by chlorine atoms introduced to the atmosphere from the release of chlorofluorocarbons. These chlorofluorocarbons were used as propellants in aerosols, as blowing agents for foams, as refrigerants and as cleaning/drying solvent systems. Because of the great chemical stability of fully halogenated chlorofluorocarbons, according to the ozone depletion theory, these compounds do not decompose in the Earth's troposphere but reach the stratosphere where they slowly degrade liberating chlorine atoms which in turn react with the ozone.

Concern reached such a level that in 1978 the U.S. Environmental Protection Agency (EPA) placed a ban on nonessential uses of fully halogenated chlorofluorocarbons (CFC) as aerosol propellants, and in 1995 banned nonessential uses of hydrochlorofluorocarbon (HCFC) propellants.

There is also a demand for aerosol propellants which have significantly less photochemical reactivity than hydrocarbons that contribute to the formation of ambient ozone and ground level smog. These compounds are typically referred to as low-VOC (volatile organic compound) or non-VOC.

The disclosure herein relates to the discovery of compositions, which include unsaturated fluorocarbons and hydrofluorocarbons. These compositions have zero ozone depletion potential (ODP), low global warming potential (GWP) and are lower VOC than hydrocarbons. These compositions are useful as pure components or in mixtures. These compositions are used as aerosol propellants.

SUMMARY OF THE INVENTION

One aspect is for a propellant comprising at least one fluorocarbon or hydrofluorocarbon selected from the group consisting of:
(i) a hydrofluorocarbon having the formula E- or Z—$R^1CH=CHR^2$, wherein $R^1$ and $R^2$ are, independently, $C_1$ to $C_6$ perfluoroalkyl groups; or
(ii) a fluorocarbon or hydrofluorocarbon selected from the group consisting of $CF_3CF=CHF$, $CF_3CH=CF_2$, $CHF_2CF=CF_2$, $CHF_2CH=CHF$, $CF_3CF=CH_2$, $CF_3CH=CHF$, $CH_2FCF=CF_2$, $CHF_2CH=CF_2$, $CHF_2CF=CHF$, $CHF_2CF=CH_2$, $CF_3CH=CH_2$, $CH_3CF=CF_2$, $CH_2FCHCF_2$, $CH_2FCF=CHF$, $CHF_2CH=CHF$, $CF_3CF=CFCF_3$, $CF3CF_2CF=CF_2$, $CF_3CF=CHCF_3$, $CF_3CF_2CF=CH_2$, $CF_3CH=CHCF_3$, $CF_3CF_2CH=CH_2$, $CF_2=CHCF_2CF_3$, $CF_2=CFCHFCF_3$, $CF_2=CFCF_2CHF_2$, $CHF_2CH=CHCF_3$, $(CF_3)_2C=CHCF_3$, $CF_3CF=CHCF_2CF_3$, $CF_3CH=CFCF_2CF_3$, $(CF_3)_2CFCH=CH_2$, $CF_3CF_2CF_2CH=CH_2$, $CF_3(CF_2)_3CF=CF_2$, $CF_3CF_2CF=CFCF_2CF_3$, $(CF_3)_2C=C(CF_3)_2$, $(CF_3)_2CFCF=CHCF_3$, $CF_2=CFCF_2CH_2F$, $CF_2=CFCHFCHF_2$, $CH_2=C(CF_3)_2$, $CH_2CF_2CF=CF_2$, $CH_2FCF=CFCHF_2$, $CH_2FCF_2CF=CF_2$, $CF_2=C(CF_3)(CH_3)$, $CH_2=C(CHF_2)(CF_3)$, $CH_2=CHCF_2CHF_2$, $CF_2=C(CHF_2)(CH_3)$, $CHF=C(CF_3)(CH_3)$, $CH_2=C(CHF_2)_2$, $CF_3CF=CFCH_3$, $CH_3CF=CHCF_3$, $CF_2=CFCF_2CF_2CF_3$, $CHF=CFCF_2CF_2CF_3$, $CF_2=CHCF_2CF_2CF_3$, $CF_2=CFCF_2CF_2CHF_2$, $CHF_2CF=CFCF_2CF_3$, $CF_3CF=CFCF_2CHF_2$, $CF_3CF=CFCHFCF_3$, $CHF=CFCF(CF_3)_2$, $CF_2=CFCH(CF_3)_2$, $CF_3CH=C(CF_3)_2$, $CF_2=CHCF(CF_3)_2$, $CH_2=CFCF_2CF_2CF_3$, $CHF=CFCF_2CF_2CHF_2$, $CH_2=C(CF_3)CF_2CF_3$, $CF_2=CHCH(CF_3)_2$, $CHF=CHCF(CF_3)_2$, $CF_2=C(CF_3)CH_2CF_3$, $CH_2=CFCF_2CF_2CHF_2$, $CF_2=CHCF_2CH_2CF_3$, $CF_3CF=C(CF_3)(CH_3)$, $CH_2=CFCH(CF_3)_2$, $CHF=CHCH(CF_3)_2$, $CH_2FCH=C(CF_3)_2$, $CH_3CF=C(CF_3)_2$, $CH_2=CHCF_2CHFCF_3$, $CH_2C(CF_3)CH_2CF_3$, $(CF_3)_2C=CHC_2F_5$, $(CF3)_2CFCF=CHCF_3$, $CH_2=CHC(CF_3)_3$, $(CF_3)_2C=C(CH_3)(CF_3)$, $CH_2=CFCF_2CH(CF_3)_2$, $CF_3CF=C(CH_3)CF_2CF_3$, $CF_3CH=CHCH(CF_3)_2$, $CH_2=CHCF_2CF_2CHF_2$, $(CF_3)_2C=CHCF_2CH_3$, $CH_2=C(CF_3)CH_2C_2F_5$, $CH_2=CHCH_2CF_2C_2F_5$, $CH_2=CHCH_2CF_2C_2F_5$, $CF_3CF_2CF=CFC_2H_5$, $CH_2=CHCH_2CF(CF_3)_2$, $CF_3CF=CHCH(CF_3)(CH_3)$, $(CF_3)_2C=CFC_2H_5$, cyclo-$CF_2CF_2CF_2CH=CH—$, cyclo-$CF_2CF_2CH=CH—$, $CF_3CF_2CF_2C(CH_3)=CH_2$, $CF_3CF_2CF_2CH=CHCH_3$, cyclo-$CF_2CF_2CF=CF—$, cyclo-$CF_2CF=CFCF_2CF_2—$, cyclo-$CF_2CF=CFCF_2CF_2CF_2$, $CF_3CF_2CF_2CF_2CH=CH_2$, $CF_3CH=CHCF_2CF_3$, $CF_2CF_2CH=CHCF_2CF_3$, $CF_3CH=CHCF_2CF_2CF_3$, $CF_3CF=CFC_2F_5$, $CF_3CF=CFCF_2C_2F_5$, $CF_3CF_2CF=CFC_2F_5$, $CF_3CH=CFCF_2C_2F_5$, $CF_3CF=CHCF_2C_2F_5$, $CF_3CF_2CH=CFCF_2C_2F_5$, $CF_3CF_2CF=CHCF_2C_2F_5$, $C_2F_5CF_2CF=CHCH_3$, $C_2F_5CF=CHCH_3$, $(CF_3)_2C=CHCH_3$, $CF_3C(CH_3)=CHCF_3$, $CHF=CFC_2F_5$, $CHF_2CF=CFCF_3$, $(CF_3)_2C=CHF$, $CH_2FCF=CFCF_3$, $CHF=CHCF_2CF_3$, $CHF_2CH=CFCF_3$, $CHF=CFCHFCF_3$, $CF_3CH=CFCHF_2$, $CHF=CFCF_2CHF_2$, $CHF_2CF=CFCHF_2$, $CH_2CF=CFCF_3$, $CH_2FCH=CFCF_3$, $CH_2=CFCHFCF_3$, $CH_2=CFCF_2CHF_2$, $CF_3CH=CFCH_2F$, $CHF=CFCH_2CF_3$, $CHF=CHCF_2CHF_2$, $CHF=CHCF_2CHF_2$, $CHF=CFCHFCHF_2$, $CF_3CF=CHCH_3$, $CF_2=CHCF_2Br$, $CHF=CBrCHF_2$, $CHBr=CHCF_3$, $CF_3CBr=CFCF_3$, $CH_2=CBrCF_2CF_3$, $CHBr=CHCF_2CF_3$, $CH_2=CHCF_2CF_2Br$, $CH_2=CHCBrFCF_3$, $CH_3CBr=CHCF_3$, $CF_3CBr=CHCH_3$, $(CF_3)_2C=CHBr$, $CF_3CF=CBrCF_2CF_3$, E-$CHF_2CBr=CFC_2F_5$, Z—$CHF_2CBr=CFC_2F_5$, $CF_2=CBrCHFC_2F_5$, $(CF_3)_2CFCBr=CH_2$, $CHBr=CF(CF_2)_2CHF_2$, $CH_2=CBrCF_2C_2F_5$, $CF_2=C(CH_2Br)CF_3$, $CH_2=C$

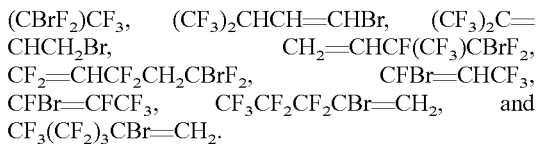
$(CBrF_2)CF_3$, $(CF_3)_2CHCH=CHBr$, $(CF_3)_2C=CHCH_2Br$, $CH_2=CHCF(CF_3)CBrF_2$, $CF_2=CHCF_2CH_2CBrF_2$, $CFBr=CHCF_3$, $CFBr=CFCF_3$, $CF_3CF_2CF_2CBr=CH_2$, and $CF_3(CF_2)_3CBr=CH_2$.

A further aspect is for a sprayable composition comprising the above-described propellant. Preferably, the sprayable composition is an aerosol.

Other objects and advantages will become apparent to those skilled in the art upon reference to the detailed description that hereinafter follows.

DETAILED DESCRIPTION OF THE INVENTION

Applicants specifically incorporate the entire content of all cited references in this disclosure. Applicants also incorporate by reference the co-owned and concurrently filed applications entitled "Fire Extinguishing and Fire Suppression Compositions Comprising Unsaturated Fluorocarbons" "Solvent Compositions Comprising Unsaturated Fluorocarbons" U.S. Application 60/732,090 filed Nov. 1, 2005, and "Blowing Agents for Forming Foam Comprising Unsaturated Fluorocarbons" U.S. Application 60/732,090 filed Nov. 1, 2005, and "Compositions Comprising Fluoroolefins and Uses Thereof", U.S. Application 60,732,581, filed Nov. 1, 2005.

Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

One aspect relates to compositions useful in aerosol; i.e., pressurized, dispensing systems. The disclosure herein relates in particular to the field of aerosol compositions which exhibit environmental responsibility while retaining desirable properties associated with aerosol dispensing systems.

There are numerous difficulties associated with formulating an environmentally responsible propellant for use with an aerosol dispensing system, including but not limited to achieving a single phase, soluble composition which will retain desirable spray characteristics and product performance characteristics of aerosols currently marketed. Flammability is also a consideration. Also problematic in the formulation of personal care products is obtaining a composition useful in dispensing active ingredient from an aerosol dispensing system absent toxic side effects.

Aerosol products are generally preferred over products dispensed by pumps or other systems. Many advantages of aerosols stem from the fact that air is not drawn into the aerosol container to replace ingredients dispensed. Thus the product is not exposed to deteriorating or oxidizing effects of air and/or transient moisture, the product maintains its sterility, and preservatives need not be included in the product composition. Consumers prefer aerosols for their convenience, ease of use and cleanliness. Broadly speaking, the characteristics of the spray dispensed from aerosol systems are superior to those of other systems. The product composition is generally applied with a finer, more even spray than when applied with pump sprays. Pump-type dispensers tend to over-concentrate the product in one spot because of inability to maintain uniformity of product dispersal throughout the target area. This is important, for example, in a hairspray product where it is desirable that the spray retain manageability and hold of the hair style yet not weigh the hair down, give an unnatural hold, or feel sticky to touch.

It is, therefore, desirable to develop a homogeneous, soluble and nontoxic composition with limited flammability, useful in an aerosol dispensing system for personal care as well as other products, which retains advantageous spray characteristics and other properties of an aerosol, while achieving environmental responsibility.

Accordingly, one aspect to provide a composition useful in an aerosol dispensing system which achieves the advantageous properties of an aerosol.

A further object to provide a sealed container with an aerosol dispensing system and a composition which attains the objectives described herein.

The foregoing objectives are achieved with the unsaturated fluorocarbon and hydrofluorocarbon propellant compositions disclosed herein. The compositions may be formulated with active ingredient from about 1-15% by weight, or more. Total propellant may vary from 15-95%.

Also contemplated is an aerosol dispensing system comprising a sealed container equipped with an aerosol dispensing valve and containing therein the composition and active ingredient as above.

An important physical property associated with the dispensing of aerosol products is the vapor pressure of the propellant. By "vapor pressure" is meant the pressure exerted when a liquefied propellant gas is in equilibrium with its vapor in a closed container, such as an aerosol can. Vapor pressure can be measured by connecting a pressure gauge to the valve on an aerosol can or gas cylinder containing the vapor/liquid mixture. A standard of measurement of vapor pressure in the U.S. aerosol industry is pounds per square inch gauge (psig) with the gas/liquefied mixture at constant temperature, most commonly at 70° F. (21° C.). The vapor pressure of liquefied gases most widely employed as aerosol propellants will vary over the range of about 20 to 90 psig (138 to 621 kPa) at 70° F. (21° C.). The propellant systems disclosed herein have vapor pressures in this range.

One aspect encompasses non-toxic compositions useful in an aerosol dispensing system. The compositions comprise unsaturated fluorocarbons (FCs) and/or hydrofluorocarbons (HFCs) alone or in mixture with each other or other suitable propellants, including saturated HFCs, hydrocarbons (HCs), dimethylether, carbon dioxide, nitrous oxide, and nitrogen. Optional active ingredients and additives may be included in the formulation in order to prepare different forms of end products by numerous methods known to those skilled in the art.

One embodiment provides blowing agents having the formula E- or Z—$R^1CH=CHR^2$ (Formula I), wherein $R^1$ and $R^2$ are, independently, $C_1$ to $C_6$ perfluoroalkyl groups. Examples of $R^1$ and $R^2$ groups include, but are not limited to, $CF_3$, $C_2F_5$, $CF_2CF_2CF_3$, $CF(CF_3)_2$, $CF_2CF_2CF_2CF_3$, $CF(CF_3)CF_2CF_3$, $CF_2CF(CF_3)_2$, $C(CF_3)_3$, $CF_2CF_2CF_2CF_2CF_3$, $CF_2CF_2CF(CF_3)_2$, $C(CF_3)_2C_2F_5$, $CF_2CF_2CF_2CF_2CF_2CF_3$, $CF(CF_3)CF_2CF_2C_2F_5$, and $C(CF_3)_2CF_2C_2F_5$. Exemplary, non-limiting Formula I compounds are presented in Table 1.

TABLE 1

| Code | Structure | Chemical Name |
|---|---|---|
| F11E | $CF_3CH=CHCF_3$ | 1,1,1,4,4,4-hexafluorobut-2-ene |
| F12E | $CF_3CH=CHC_2F_5$ | 1,1,1,4,4,5,5,5-octafluoropent-2-ene |
| F13E | $CF_3CH=CHCF_2C_2F_5$ | 1,1,1,4,4,5,5,6,6,6-decafluorohex-2-ene |
| F13iE | $CF_3CH=CHCF(CF_3)_2$ | 1,1,1,4,5,5,5-heptafluoro-4-(trifluoromethyl)pent-2-ene |
| F22E | $C_2F_5CH=CHC_2F_5$ | 1,1,1,2,2,5,5,6,6,6-decafluorohex-3-ene |
| F14E | $CF_3CH=CH(CF_2)_3CF_3$ | 1,1,1,4,4,5,5,6,6,7,7,7-dodecafluorohept-2-ene |
| F14iE | $CF_3CH=CHCF_2CF—(CF_3)_2$ | 1,1,1,4,4,5,6,6,6-nonafluoro-5-(trifluoromethyl)hex-2-ene |
| F14sE | $CF_3CH=CHCF(CF_3)—C_2F_5$ | 1,1,1,4,5,5,6,6,6-nonfluoro-4-(trifluoromethyl)hex-2-ene |
| F14tE | $CF_3CH=CHC(CF_3)_3$ | 1,1,1,5,5,5-hexafluoro-4,4-bis(trifluoromethyl)pent-2-ene |
| F23E | $C_2F_5CH=CHCF_2C_2F_5$ | 1,1,1,2,2,5,5,6,6,7,7,7-dodecafluorohept-3-ene |
| F23iE | $C_2F_5CH=CHCF(CF_3)_2$ | 1,1,1,2,2,5,6,6,6-nonafluoro-5-(trifluoromethyl)hex-3-ene |
| F15E | $CF_3CH=CH(CF_2)_4CF_3$ | 1,1,1,4,4,5,5,6,6,7,7,8,8,8-tetradecafluorooct-2-ene |
| F15iE | $CF_3CH=CH—CF_2CF_2CF(CF_3)_2$ | 1,1,1,4,4,5,5,6,7,7,7-undecafluoro-6-(trifluoromethyl)hept-2-ene |
| F15tE | $CF_3CH=CH—C(CF_3)_2C_2F_5$ | 1,1,1,5,5,6,6,6-octafluoro-4,4-bis(trifluoromethyl)hex-2-ene |
| F24E | $C_2F_5CH=CH(CF_2)_3CF_3$ | 1,1,1,2,2,5,5,6,6,7,7,8,8,8-tetradecafluorooct-3-ene |
| F24iE | $C_2F_5CH=CHCF_2CF—(CF_3)_2$ | 1,1,1,2,2,5,5,6,7,7,7-undecafluoro-6-(trifluoromethyl)hept-3-ene |
| F24sE | $C_2F_5CH=CHCF(CF_3)—C_2F_5$ | 1,1,1,2,2,5,6,6,7,7,7-undecafluoro-5-(trifluoromethyl)hept-3-ene |
| F24tE | $C_2F_5CH=CHC(CF_3)_3$ | 1,1,1,2,2,6,6,6-octafluoro-5,5-bis(trifluoromethyl)hex-3-ene |
| F33E | $C_2F_5CF_2CH=CH—CF_2C_2F_5$ | 1,1,1,2,2,3,3,6,6,7,7,8,8,8-tetradecafluorooct-4-ene |
| F3i3iE | $(CF_3)_2CFCH=CH—CF(CF_3)_2$ | 1,1,1,2,5,6,6,6-octafluoro-2,5-bis(trifluoromethyl)hex-3-ene |
| F33iE | $C_2F_5CF_2CH=CH—CF(CF_3)_2$ | 1,1,1,2,5,5,6,6,7,7,7-undecafluoro-2-(trifluoromethyl)hept-3-ene |
| F16E | $CF_3CH=CH(CF_2)_5CF_3$ | 1,1,1,4,4,5,5,6,6,7,7,8,8,,9,9,9-hexadecafluoronon-2-ene |
| F16sE | $CF_3CH=CHCF(CF_3)—(CF_2)_2C_2F_5$ | 1,1,1,4,5,5,6,6,7,7,8,8,8-tridecafluoro-4-(trifluoromethyl)hept-2-ene |
| F16tE | $CF_3CH=CHC(CF_3)_2—CF_2C_2F_5$ | 1,1,1,6,6,6-octafluoro-4,4-bis(trifluoromethyl)hept-2-ene |
| F25E | $C_2F_5CH=CH(CF_2)_4CF_3$ | 1,1,1,2,2,5,5,6,6,7,7,8,8,9,9,9-hexadecafluoronon-3-ene |
| F25iE | $C_2F_5CH=CH—CF_2CF_2CF(CF_3)_2$ | 1,1,1,2,2,5,5,6,6,7,8,8,8-tridecafluoro-7-(trifluoromethyl)oct-3-ene |
| F25tE | $C_2F_5CH=CH—C(CF_3)_2C_2F_5$ | 1,1,1,2,2,6,6,7,7-decafluoro-5,5-bis(trifluoromethyl)hept-3-ene |
| F34E | $C_2F_5CF_2CH=CH—(CF_2)_3CF_3$ | 1,1,1,2,2,3,3,6,6,7,7,8,8,9,9,9-hexadecafluoronon-4-ene |
| F34iE | $C_2F_5CF_2CH=CH—CF_2CF(CF_3)_2$ | 1,1,1,2,2,3,3,6,6,7,8,8,8-tridecafluoro-7-(trifluoromethyl)oct-4-ene |
| F34sE | $C_2F_5CF_2CH=CH—CF(CF_3)C_2F_5$ | 1,1,1,2,2,3,3,6,7,7,8,8,8-tridecafluoro-6-(trifluoromethyl)oct-4-ene |
| F34tE | $C_2F_5CF_2CH=CH—C(CF_3)_3$ | 1,1,1,5,5,6,6,7,7,7-decafluoro-2,2-bis(trifluoromethyl)hept-3-ene |
| F3i4E | $(CF_3)_2CFCH=CH—(CF_2)_3CF_3$ | 1,1,1,2,5,5,6,6,7,7,8,8,8-tridecafluoro-2(trifluoromethyl)oct-3-ene |
| F3i4iE | $(CF_3)_2CFCH=CH—CF_2CF(CF_3)_2$ | 1,1,1,2,5,5,6,6,7,7,7-decafluoro-2,6-bis(trifluoromethyl)hept-3-ene |
| F3i4sE | $(CF_3)_2CFCH=CH—CF(CF_3)C_2F_5$ | 1,1,1,2,5,6,6,7,7,7-decafluoro-2,5-bis(trifluoromethyl)hept-3-ene |
| F3i4tE | $(CF_3)_2CFCH=CH—C(CF_3)_3$ | 1,1,1,2,6,6,6-heptafluoro-2,5,5-tris(trifluoromethyl)hex-3-ene |
| F26E | $C_2F_5CH=CH(CF_2)_5CF_3$ | 1,1,1,2,2,5,5,6,6,7,7,8,8,9,9,10,10,10-octadecafluorodec-3-ene |
| F26sE | $C_2F_5CH=CHCF(CF_3)—(CF_2)_2C_2F_5$ | 1,1,1,2,2,5,6,6,7,7,8,8,9,9,9-pentadecafluoro-5-(trifluoromethyl)non-3-ene |
| F26tE | $C_2F_5CH=CHC(CF_3)_2—CF_2C_2F_5$ | 1,1,1,2,2,6,6,7,7,8,8-dodecafluoro-5,5-bis(trifluoromethyl)oct-3-ene |
| F35E | $C_2F_5CF_2CH=CH—(CF_2)_4CF_3$ | 1,1,1,2,2,3,3,6,6,7,7,8,8,9,9,10,10,10-octadecafluorodec-4-ene |
| F35iE | $C_2F_5CF_2CH=CH—CF_2CF_2CF(CF_3)_2$ | 1,1,1,2,2,3,3,6,6,7,8,8,9,9,9-pentadecafluoro-8-(trifluoromethyl)non-4-ene |
| F35tE | $C_2F_5CF_2CH=CH—C(CF_3)_2C_2F_5$ | 1,1,1,2,2,3,3,7,7,8,8,8-dodecafluoro-6,6-bis(trifluoromethyl)oct-4-ene |
| F3i5E | $(CF_3)_2CFCH=CH—(CF_2)_4CF_3$ | 1,1,1,2,5,5,6,6,7,7,8,8,9,9,9-pentadecafluoro-2-(trifluoromethyl)non-3-ene |
| F3i5iE | $(CF_3)_2CFCH=CH—CF_2CF_2CF(CF_3)_2$ | 1,1,1,2,5,5,6,6,7,8,8,8-dodecafluoro-2,7-bis(trifluoromethyl)oct-3-ene |
| F3i5tE | $(CF_3)_2CFCH=CH—C(CF_3)_2C_2F_5$ | 1,1,1,2,6,6,7,7,7-nonafluoro-2,5,5-tris(trifluoromethyl)hept-3-ene |
| F44E | $CF_3(CF_2)_3CH=CH—(CF_2)_3CF_3$ | 1,1,1,2,2,3,3,4,4,7,7,8,8,9,9,10,10,10-octadecafluorodec-5-ene |
| F44iE | $CF_3(CF_2)_3CH=CH—CF_2CF(CF_3)_2$ | 1,1,1,2,3,3,6,6,7,7,8,8,9,9,9-pentadecafluoro-2-(trifluoromethyl)non-4-ene |
| F44sE | $CF_3(CF_2)_3CH=CH—CF(CF_3)C_2F_5$ | 1,1,1,2,2,3,6,6,7,7,8,8,9,9,9-pentadecafluoro-3-(trifluoromethyl)non-4-ene |
| F44tE | $CF_3(CF_2)_3CH=CH—C(CF_3)_3$ | 1,1,1,5,5,6,6,7,7,8,8,8-dodecafluoro-2,2,-bis(trifluoromethyl)oct-3-ene |
| F4i4iE | $(CF_3)_2CFCF_2CH=CH—CF_2CF(CF_3)_2$ | 1,1,1,2,3,3,6,6,7,7,8,8,8-dodecafluoro-2,7-bis(trifluoromethyl)oct-4-ene |
| F4i4sE | $(CF_3)_2CFCF_2CH=CH—CF(CF_3)C_2F_5$ | 1,1,1,2,3,3,6,7,7,8,8,8-dodecafluoro-2,6-bis(trifluoromethyl)oct-4-ene |
| F4i4tE | $(CF_3)_2CFCF_2CH=CH—C(CF_3)_3$ | 1,1,1,5,5,6,7,7,7-nonafluoro-2,2,6-tris(trifluoromethyl)hept-3-ene |
| F4s4sE | $C_2F_5CF(CF_3)CH=CH—CF(CF_3)C_2F_5$ | 1,1,1,2,2,3,6,7,7,8,8,8-dodecafluoro-3,6-bis(trifluoromethyl)oct-4-ene |
| F4s4tE | $C_2F_5CF(CF_3)CH=CH—C(CF_3)_3$ | 1,1,1,5,6,6,7,7,7-nonafluoro-2,2,5-tris(trifluoromethyl)hept-3-ene |
| F4t4tE | $(CF_3)_3CCH=CH—C(CF_3)_3$ | 1,1,1,6,6,6-hexafluoro-2,2,5,5-tetrakis(trifluoromethyl)hex-3-ene |

Compounds of Formula I may be prepared by contacting a perfluoroalkyl iodide of the formula $R^1I$ with a perfluoroalkyltrihydroolefin of the formula $R^2CH=CH_2$ to form a trihydroiodoperfluoroalkane of the formula $R^1CH_2CHIR^2$. This trihydroiodoperfluoroalkane can then be dehydroiodinated to form $R^1CH=CHR^2$. Alternatively, the olefin $R^1CH=CHR^2$ may be prepared by dehydroiodination of a trihydroiodoperfluoroalkane of the formula $R^1CHICH_2R^2$ formed in turn by reacting a perfluoroalkyl iodide of the formula $R^2I$ with a perfluoroalkyltrihydroolefin of the formula $R^1CH=CH_2$.

Said contacting of a perfluoroalkyl iodide with a perfluoroalkyltrihydroolefin may take place in batch mode by combining the reactants in a suitable reaction vessel capable of operating under the autogenous pressure of the reactants and products at reaction temperature. Suitable reaction vessels include fabricated from stainless steels, in particular of the austenitic type, and the well-known high nickel alloys such as Monel® nickel-copper alloys, Hastelloy® nickel based alloys and Inconel® nickel-chromium alloys.

Alternatively, the reaction may take be conducted in semi-batch mode in which the perfluoroalkyltrihydroolefin reactant is added to the perfluoroalkyl iodide reactant by means of a suitable addition apparatus such as a pump at the reaction temperature.

The ratio of perfluoroalkyl iodide to perfluoroalkyltrihydroolefin should be between about 1:1 to about 4:1, preferably from about 1.5:1 to 2.5:1. Ratios less than 1.5:1 tend to result in large amounts of the 2:1 adduct as reported by Jeanneaux, et al. in Journal of Fluorine Chemistry, Vol. 4, pages 261-270 (1974).

Preferred temperatures for contacting of said perfluoroalkyl iodide with said perfluoroalkyltrihydroolefin are preferably within the range of about 150° C. to 300° C., preferably from about 170° C. to about 250° C., and most preferably from about 180° C. to about 230° C.

Suitable contact times for the reaction of the perfluoroalkyl iodide with the perfluoroalkyltrihydroolefin are from about 0.5 hour to 18 hours, preferably from about 4 to about 12 hours.

The trihydroiodoperfluoroalkane prepared by reaction of the perfluoroalkyl iodide with the perfluoroalkyltrihydroolefin may be used directly in the dehydroiodination step or may preferably be recovered and purified by distilled prior to the dehydroiodination step.

The dehydroiodination step is carried out by contacting the trihydroiodoperfluoroalkane with a basic substance. Suitable basic substances include alkali metal hydroxides (e.g., sodium hydroxide or potassium hydroxide), alkali metal oxide (for example, sodium oxide), alkaline earth metal hydroxides (e.g., calcium hydroxide), alkaline earth metal oxides (e.g., calcium oxide), alkali metal alkoxides (e.g., sodium methoxide or sodium ethoxide), aqueous ammonia, sodium amide, or mixtures of basic substances such as soda lime. Preferred basic substances are sodium hydroxide and potassium hydroxide.

Said contacting of the trihydroiodoperfluoroalkane with a basic substance may take place in the liquid phase preferably in the presence of a solvent capable of dissolving at least a portion of both reactants. Solvents suitable for the dehydroiodination step include one or more polar organic solvents such as alcohols (e.g., methanol, ethanol, n-propanol, isopropanol, n-butanol, isobutanol, and tertiary butanol), nitriles (e.g., acetonitrile, propionitrile, butyronitrile, benzonitrile, or adiponitrile), dimethyl sulfoxide, N,N-dimethylformamide, N,N-dimethylacetamide, or sulfolane. The choice of solvent may depend on the boiling point product and the ease of separation of traces of the solvent from the product during purification. Typically, ethanol or isopropanol are good solvents for the reaction.

Typically, the dehydroiodination reaction may be carried out by addition of one of the reactants (either the basic substance or the trihydroiodoperfluoroalkane) to the other reactant in a suitable reaction vessel. Said reaction may be fabricated from glass, ceramic, or metal and is preferably agitated with an impellor or stirring mechanism.

Temperatures suitable for the dehydroiodination reaction are from about 10° C. to about 100° C., preferably from about 20° C. to about 70° C. The dehydroiodination reaction may be carried out at ambient pressure or at reduced or elevated pressure. Of note are dehydroiodination reactions in which the compound of Formula I is distilled out of the reaction vessel as it is formed.

Alternatively, the dehydroiodination reaction may be conducted by contacting an aqueous solution of said basic substance with a solution of the trihydroiodoperfluoroalkane in one or more organic solvents of lower polarity such as an alkane (e.g., hexane, heptane, or octane), aromatic hydrocarbon (e.g., toluene), halogenated hydrocarbon (e.g., methylene chloride, ethylene dichloride, chloroform, carbon tetrachloride, or perchloroethylene), or ether (e.g., diethyl ether, methyl tert-butyl ether, tetrahydrofuran, 2-methyl tetrahydrofuran, dioxane, dimethoxyethane, diglyme, or tetraglyme) in the presence of a phase transfer catalyst. Suitable phase transfer catalysts include quaternary ammonium halides (e.g., tetrabutylammonium bromide, tetrabutylammonium hydrosulfate, triethylbenzylammonium chloride, dodecyltrimethylammonium chloride, and tricaprylylmethylammonium chloride), quaternary phosphonium halides (e.g., triphenylmethylphosphonium bromide and tetraphenylphosphonium chloride), cyclic ether compounds known in the art as crown ethers (e.g., 18-crown-6 and 15-crown-5).

Alternatively, the dehydroiodination reaction may be conducted in the absence of solvent by adding the trihydroiodoperfluoroalkane to a solid or liquid basic substances.

Suitable reaction times for the dehydroiodination reactions are from about 15 minutes to about six hours or more depending on the solubility of the reactants. Typically the dehydroiodination reaction is rapid and requires about 30 minutes to about three hours for completion.

The compound of formula I may be recovered from the dehydroiodination reaction mixture by phase separation after addition of water, by distillation, or by a combination thereof.

The compositions disclosed herein may comprise a single compound of Formula I, for example, one of the compounds in Table 1, or may comprise a combination of compounds of Formula I.

In addition to the inventive compounds described above, compounds presented in Table 2 can be used as aerosol propellants.

TABLE 2

| Name | Structure | Chemical name |
|---|---|---|
| HFC-1225s | $C_3HF_5$ | |
| HFC-1225ye | $CF_3CF=CHF$ | 1,2,3,3,3-pentafluoro-1-propene |
| HFC-1225zc | $CF_3CH=CF_2$ | 1,1,3,3,3-pentafluoro-1-propene |
| HFC-1225yc | $CHF_2CF=CF_2$ | 1,1,2,3,3-pentafluoro-1-propene |
| HFC-1234s | $C_3H_2F_4$ | |
| HFC-1234ye | $CHF_2CF=CHF$ | 1,2,3,3-tetrafluoro-1-propene |
| HFC-1234yf | $CF_3CF=CH_2$ | 2,3,3,3-tetrafluoro-1-propene |
| HFC-1234ze | $CF_3CH=CHF$ | 1,3,3,3-tetrafluoro-1-propene |
| HFC-1234yc | $CH_2FCF=CF_2$ | 1,1,2,3-tetrafluoro-1-propene |
| HFC-1234zc | $CHF_2CH=CF_2$ | 1,1,3,3-tetrafluoro-1-propene |
| HFC-1234ye | $CHF_2CF=CHF$ | 1,2,3,3-tetrafluoro-1-propene |
| HFC-1243s | $C_3H_3F_3$ | |
| HFC-1243yf | $CHF_2CF=CH_2$ | 2,3,3-trifluoro-1-propene |
| HFC-1243zf | $CF_3CH=CH_2$ | 3,3,3-trifluoro-1-propene |
| HFC-1243yc | $CH_3CF=CF_2$ | 1,1,2-trifluoro-1-propene |
| HFC-1243zc | $CH_2FCH=CF_2$ | 1,1,3-trifluoro-1-propene |
| HFC-1243ye | $CHF_2CF=CHF$ | 1,2,3-trifluoro-1-propene |
| HFC-1243ze | $CHF_2CH=CHF$ | 1,3,3-trifluoro-1-propene |
| FC-1318s | $C_4F_8$ | |
| FC-1318my | $CF_3CF=CFCF_3$ | 1,1,1,2,3,4,4,4-octafluoro-2-butene |
| FC-1318cy | $CF_3CF_2CF=CF_2$ | 1,1,2,3,3,4,4,4-octafluoro-1-butene |
| HFC-1327s | $C_4HF_7$ | |
| HFC-1327my | $CF_3CF=CHCF_3$ | 1,1,1,2,4,4,4-heptafluoro-2-butene |
| HFC-1327ye | $CHF=CFCF_2CF_3$ | 1,2,3,3,4,4,4-heptafluoro-1-butene |

TABLE 2-continued

| Name | Structure | Chemical name |
|---|---|---|
| HFC-1327py | CHF$_2$CF=CFCF$_3$ | 1,1,1,2,3,4,4-heptafluoro-2-butene |
| HFC-1327et | (CF$_3$)$_2$C=CHF | 1,3,3,3-tetrafluoro-2-(trifluoromethyl)-1-propene |
| HFC-1327cz | CF$_2$=CHCF$_2$CF$_3$ | 1,1,3,3,4,4,4-heptafluoro-1-butene |
| HFC-1327cye | CF$_2$=CFCHFCF$_3$ | 1,1,2,3,4,4,4-heptafluoro-1-butene |
| HFC-1327cyc | CF$_2$=CFCF$_2$CHF$_2$ | 1,1,2,3,3,4,4-heptafluoro-1-butene |
| HFC-1336s | C$_4$H$_2$F$_6$ | |
| HFC-1336yf | CF$_3$CF$_2$CF=CH$_2$ | 2,3,3,4,4,4-hexafluoro-1-butene |
| HFC-1336ze | CHF=CHCF$_2$CF$_3$ | 1,3,3,4,4,4-hexafluoro-1-butene |
| HFC-1336eye | CHF=CFCHFCF$_3$ | 1,2,3,4,4,4-hexafluoro-1-butene |
| HFC-1336eyc | CHF=CFCF$_2$CHF$_2$ | 1,2,3,3,4,4-hexafluoro-1-butene |
| HFC-1336pyy | CHF$_2$CF=CFCHF$_2$ | 1,1,2,3,4,4-hexafluoro-2-butene |
| HFC-1336qy | CH$_2$FCF=CFCF$_3$ | 1,1,1,2,3,4-hexafluoro-2-butene |
| HFC-1336pz | CHF$_2$CH=CFCF$_3$ | 1,1,1,2,4,4-hexafluoro-2-butene |
| HFC-1336mzy | CF$_3$CH=CFCHF$_2$ | 1,1,1,3,4,4-hexafluoro-2-butene |
| HFC-1336qc | CF$_2$=CFCF$_2$CH$_2$F | 1,1,2,3,3,4-hexafluoro-1-butene |
| HFC-1336pe | CF$_2$=CFCHFCHF$_2$ | 1,1,2,3,4,4-hexafluoro-1-butene |
| HFC-1336ft | CH$_2$=C(CF$_3$)$_2$ | 3,3,3-trifluoro-2-(trifluoromethyl)-1-propene |
| HFC-1345s | C$_4$H$_3$F$_5$ | |
| HFC-1345qz | CH$_2$FCH=CFCF$_3$ | 1,1,1,2,4-pentafluoro-2-butene |
| HFC-1345mzy | CF$_3$CH=CFCH$_2$F | 1,1,1,3,4-pentafluoro-2-butene |
| HFC-1345fz | CF$_3$CF$_2$CH=CH$_2$ | 3,3,4,4,4-pentafluoro-1-butene |
| HFC-1345mzz | CHF$_2$CH=CHCF$_3$ | 1,1,1,4,4-pentafluoro-2-butene |
| HFC-1345sy | CH$_3$CF=CFCF$_3$ | 1,1,1,2,3-pentafluoro-2-butene |
| HFC-1345fyc | CH$_2$=CFCF$_2$CHF$_2$ | 2,3,3,4,4-pentafluoro-1-butene |
| HFC-1345pyz | CHF$_2$CF=CHCHF$_2$ | 1,1,2,4,4-pentafluoro-2-butene |
| HFC-1345cyc | CH$_3$CF$_2$CF=CF$_2$ | 1,1,2,3,3-pentafluoro-1-butene |
| HFC-1345pyy | CH$_2$FCF=CFCHF$_2$ | 1,1,2,3,4-pentafluoro-2-butene |
| HFC-1345eyc | CH$_2$FCF$_2$CF=CF$_2$ | 1,2,3,3,4-pentafluoro-1-butene |
| HFC-1345ctm | CF$_2$=C(CF$_3$)(CH$_3$) | 1,1,3,3,3-pentafluoro-2-methyl-1-propene |
| HFC-1345ftp | CH$_2$=C(CHF$_2$)(CF$_3$) | 2-(difluoromethyl)-3,3,3-trifluoro-1-propene |
| HFC-1354s | C$_4$H$_4$F$_4$ | |
| HFC-1354fzc | CH$_2$=CHCF$_2$CHF$_2$ | 3,3,4,4-tetrafluoro-1-butene |
| HFC-1354ctp | CF$_2$=C(CHF$_2$)(CH$_3$) | 1,1,3,3-tetrafluoro-2-methyl-1-propene |
| HFC-1354etm | CHF=C(CF$_3$)(CH$_3$) | 1,3,3,3-tetrafluoro-2-methyl-1-propene |
| HFC-1354tfp | CH$_2$=C(CHF$_2$)$_2$ | 2-(difluoromethyl)-3,3-difluoro-1-propene |
| HFC-1354my | CF$_3$CF=CFCH$_3$ | 1,1,1,2-tetrafluoro-2-butene |
| HFC-1354mzy | CH$_3$CF=CHCF$_3$ | 1,1,1,3-tetrafluoro-2-butene |
| FC-141-10s | C$_5$F$_{10}$ | |
| FC-141-10myy | CF$_3$CF=CFCF$_2$CF$_3$ | 1,1,1,2,3,4,4,5,5,5-decafluoro-2-pentene |
| FC-141-10cy | CF$_2$=CFCF$_2$CF$_2$CF$_3$ | 1,1,2,3,3,4,4,5,5,5-decafluoro-1-pentene |
| HFC-1429s | C$_5$HF$_9$ | |
| HFC-1429mzt | (CF$_3$)$_2$C=CHCF$_3$ | 1,1,1,4,4,4-hexafluoro-2-(trifluoromethyl)-2-butene |
| HFC-1429myz | CF$_3$CF=CHCF$_2$CF$_3$ | 1,1,1,2,4,4,5,5,5-nonafluoro-2-pentene |
| HFC-1429mzy | CF$_3$CH=CFCF$_2$CF$_3$ | 1,1,1,3,4,4,5,5,5-nonafluoro-2-pentene |
| HFC-1429eyc | CHF=CFCF$_2$CF$_2$CF$_3$ | 1,2,3,3,4,4,5,5,5-nonafluoro-1-pentene |
| HFC-1429czc | CF$_2$=CHCF$_2$CF$_2$CF$_3$ | 1,1,3,3,4,4,5,5,5-nonafluoro-1-pentene |
| HFC-1429cycc | CF$_2$=CFCF$_2$CF$_2$CHF$_2$ | 1,1,2,3,3,4,4,5,5-nonafluoro-1-pentene |
| HFC-1429pyy | CHF$_2$CF=CFCF$_2$CF$_3$ | 1,1,2,3,4,4,5,5,5-nonafluoro-2-pentene |
| HFC-1429myyc | CF$_3$CF=CFCF$_2$CHF$_2$ | 1,1,1,2,3,4,4,5,5-nonafluoro-2-pentene |
| HFC-1429myye | CF$_3$CF=CFCHFCF$_3$ | 1,1,1,2,3,4,5,5,5-nonafluoro-2-pentene |
| HFC-1429eyym | CHF=CFCF(CF$_3$)$_2$ | 1,2,3,4,4,4-hexafluoro-3-(trifluoromethyl)-1-butene |
| HFC-1429cyzm | CF$_2$=CFCH(CF$_3$)$_2$ | 1,1,2,4,4,4-hexafluoro-3-(trifluoromethyl)-1-butene |
| HFC-1429mzt | CF$_3$CH=C(CF$_3$)$_2$ | 1,1,1,4,4,4-hexafluoro-3-(trifluoromethyl)-2-butene |
| HFC-1429czym | CF$_2$=CHCF(CF$_3$)$_2$ | 1,1,3,4,4,4-hexafluoro-3-(trifluoromethyl)-1-butene |

TABLE 2-continued

| Name | Structure | Chemical name |
|---|---|---|
| HFC-1438s | $C_5H_2F_8$ | |
| HFC-1438fy | $CH_2=CFCF_2CF_2CF_3$ | 2,3,3,4,4,5,5,5-octafluoro-1-pentene |
| HFC-1438eycc | $CHF=CFCF_2CF_2CHF_2$ | 1,2,3,3,4,4,5,5-octafluoro-1-pentene |
| HFC-1438ftmc | $CH_2=C(CF_3)CF_2CF_3$ | 3,3,4,4-pentafluoro-2-(trifluoromethyl)-1-butene |
| HFC-1438czzm | $CF_2=CHCH(CF_3)_2$ | 1,1,4,4,4-pentafluoro-3-(trifluoromethyl)-1-butene |
| HFC-1438ezym | $CHF=CHCF(CF_3)_2$ | 1,3,4,4,4-pentafluoro-3-(trifluoromethyl)-1-butene |
| HFC-1438ctmf | $CF_2=C(CF_3)CH_2CF_3$ | 1,1,4,4,4-pentafluoro-2-(trifluoromethyl)-1-butene |
| HFC-1447s | $C_5H_3F_7$ | |
| HFC-1447fzy | $(CF_3)_2CFCH=CH_2$ | 3,4,4,4-tetrafluoro-3-(trifluoromethyl)-1-butene |
| HFC-1447fz | $CF_3CF_2CF_2CH=CH_2$ | 3,3,4,4,5,5,5-heptafluoro-1-pentene |
| HFC-1447fycc | $CH_2=CFCF_2CF_2CHF_2$ | 2,3,3,4,4,5,5-heptafluoro-1-pentene |
| HFC-1447czcf | $CF_2=CHCF_2CH_2CF_3$ | 1,1,3,3,5,5,5-heptafluoro-1-pentene |
| HFC-1447mytm | $CF_3CF=C(CF_3)(CH_3)$ | 1,1,1,2,4,4,4-heptafluoro-3-methyl-2-butene |
| HFC-1447fyz | $CH_2=CFCH(CF_3)_2$ | 2,4,4,4-tetrafluoro-3-(trifluoromethyl)-1-butene |
| HFC-1447ezz | $CHF=CHCH(CF_3)_2$ | 1,4,4,4-tetrafluoro-3-(trifluoromethyl)-1-butene |
| HFC-1447qzt | $CH_2FCH=C(CF_3)_2$ | 1,4,4,4-tetrafluoro-3-(trifluoromethyl)-2-butene |
| HFC-1447syt | $CH_3CF=C(CF_3)_2$ | 2,4,4,4-tetrafluoro-3-(trifluoromethyl)-2-butene |
| HFC-1456s | $C_5H_4F_6$ | |
| HFC-1456szt | $(CF_3)_2C=CHCH_3$ | 3-(trifluoromethyl)-4,4,4-trifluoro-2-butene |
| HFC-1456szy | $CF_3CF_2CF=CHCH_3$ | 3,4,4,5,5,5-hexafluoro-2-pentene |
| HFC-1456mstz | $CF_3C(CH_3)=CHCF_3$ | 1,1,1,4,4,4-hexafluoro-2-methyl-2-butene |
| HFC-1456fzce | $CH_2=CHCF_2CHFCF_3$ | 3,3,4,5,5,5-hexafluoro-1-pentene |
| HFC-1456ftmf | $CH_2=C(CF_3)CH_2CF_3$ | 4,4,4-trifluoro-2-(trifluoromethyl)-1-butene |
| FC-151-12s | $C_6F_{12}$ | |
| FC-151-12c | $CF_3(CF_2)_3CF=CF_2$ | 1,1,2,3,3,4,4,5,5,6,6,6-dodecafluoro-1-hexene (or perfluoro-1-hexene) |
| FC-151-12mcy | $CF_3CF_2CF=CFCF_2CF_3$ | 1,1,1,2,2,3,4,5,5,6,6,6-dodecafluoro-3-hexene (or perfluoro-3-hexene) |
| FC-151-12mmtt | $(CF_3)_2C=C(CF_3)_2$ | 1,1,1,4,4,4-hexafluoro-2,3-bis(trifluoromethyl)-2-butene |
| FC-151-12mmzz | $(CF_3)_2CFCF=CFCF_3$ | 1,1,1,2,3,4,5,5,5-nonafluoro-4-(trifluoromethyl)-2-pentene |
| HFC-152-11s | $C_6HF_{11}$ | |
| HFC-152-11mmtz | $(CF_3)_2C=CHC_2F_5$ | 1,1,1,4,4,5,5,5-octafluoro-2-(trifluoromethyl)-2-pentene |
| HFC-152-11mmyyz | $(CF_3)_2CFCF=CHCF_3$ | 1,1,1,3,4,5,5,5-octafluoro-4-(trifluoromethyl)-2-pentene |
| HFC-1549s | $C_6H_3F_9$ | |
| PFBE (or HFC-1549fz) | $CF_3CF_2CF_2CF_2CH=CH_2$ | 3,3,4,4,5,5,6,6,6-nonafluoro-1-hexene (or perfluorobutylethylene) |
| HFC-1549fztmm | $CH_2=CHC(CF_3)_3$ | 4,4,4-trifluoro-3,3-bis(trifluoromethyl)-1-butene |
| HFC-1549mmtts | $(CF_3)_2C=C(CH_3)(CF_3)$ | 1,1,1,4,4,4-hexafluoro-3-methyl-2-(trifluoromethyl)-2-butene |
| HFC-1549fycz | $CH_2=CFCF_2CH(CF_3)_2$ | 2,3,3,5,5,5-hexafluoro-4-(trifluoromethyl)-1-pentene |
| HFC-1549myts | $CF_3CF=C(CH_3)CF_2CF_3$ | 1,1,1,2,4,4,5,5,5-nonafluoro-3-methyl-2-pentene |
| HFC-1549mzzz | $CF_3CH=CHCH(CF_3)_2$ | 1,1,1,5,5,5-hexafluoro-4-(trifluoromethyl)-2-pentene |
| HFC-1558s | $C_6H_4F_8$ | |
| HFC-1558szy | $CF_3CF_2CF_2CF=CHCH_3$ | 3,4,4,5,5,6,6,6-octafluoro-2-hexene |
| HFC-1558fzccc | $CH_2=CHCF_2CF_2CF_2CHF_2$ | 3,3,4,4,5,5,6,6-octafluoro-2-hexene |
| HFC-1558mmtzc | $(CF_3)_2C=CHCF_2CH_3$ | 1,1,1,4,4-pentafluoro-2-(trifluoromethyl)-2-pentene |
| HFC-1558ftmf | $CH_2=C(CF_3)CH_2C_2F_5$ | 4,4,5,5,5-pentafluoro-2-(trifluoromethyl)-1-pentene |
| HFC-1567s | $C_6H_5F_7$ | |
| HFC-1567fts | $CF_3CF_2CF_2C(CH_3)=CH_2$ | 3,3,4,4,5,5,5-heptafluoro-2-methyl-1-pentene |
| HFC-1567szz | $CF_3CF_2CF_2CH=CHCH_3$ | 4,4,5,5,6,6,6-heptafluoro-2-hexene |
| HFC-1567fzfc | $CH_2=CHCH_2CF_2C_2F_5$ | 4,4,5,5,6,6,6-heptafluoro-1-hexene |
| HFC-1567sfyy | $CF_3CF_2CF=CFC_2H_5$ | 1,1,1,2,2,3,4-heptafluoro-3-hexene |
| HFC-1567fzfy | $CH_2=CHCH_2CF(CF_3)_2$ | 4,5,5,5-tetrafluoro-4-(trifluoromethyl)-1-pentene |

TABLE 2-continued

| Name | Structure | Chemical name |
|---|---|---|
| HFC-1567myzzm | $CF_3CF=CHCH(CF_3)(CH_3)$ | 1,1,1,2,5,5,5-heptafluoro-4-methyl-2-pentene |
| HFC-1567mmtyf | $(CF_3)_2C=CFC_2H_5$ | 1,1,1,3-tetrafluoro-2-(trifluoromethyl)-2-pentene |
| FC-161-14s | $C_7F_{14}$ | |
| FC-161-14myy | $CF_3CF=CFCF_2CF_2C_2F_5$ | 1,1,1,2,3,4,4,5,5,6,6,7,7,7-tetradecafluoro-2-heptene |
| FC-161-14mcyy | $CF_3CF_2CF=CFCF_2C_2F_5$ | 1,1,1,2,2,3,4,5,5,6,6,7,7,7-tetradecafluoro-2-heptene |
| HFCs-162-13s | $C_7HF_{13}$ | |
| HFC-162-13mzy | $CF_3CH=CFCF_2CF_2C_2F_5$ | 1,1,1,3,4,4,5,5,6,6,7,7,7-tridecafluoro-2-heptene |
| HFC162-13myz | $CF_3CF=CHCF_2CF_2C_2F_5$ | 1,1,1,2,4,4,5,5,6,6,7,7,7-tridecafluoro-2-heptene |
| HFC-162-13mczy | $CF_3CF_2CH=CFCF_2C_2F_5$ | 1,1,1,2,2,4,5,5,6,6,7,7,7-tridecafluoro-3-heptene |
| HFC-162-13mcyz | $CF_3CF_2CF=CHCF_2C_2F_5$ | 1,1,1,2,2,3,5,5,6,6,7,7,7-tridecafluoro-3-heptene |
| Cyclic fluoroolefins | $Cyclo[-CX=CY(CXY)_n-]$ | |
| HFC-C1316cc | cyclo-$CF_2CF_2CF=CF-$ | 1,2,3,3,4,4-hexafluorocyclobutene |
| HFC-C1334cc | cyclo-$CF_2CF_2CH=CH-$ | 3,3,4,4-tetrafluorocyclobutene |
| HFC-C1436 | cyclo-$CF_2CF_2CF_2CH=CH-$ | 3,3,4,4,5,5,-hexafluorocyclopentene |
| HFC-C1418y | cyclo-$CF_2CF=CFCF_2CF_2-$ | 1,2,3,3,4,4,5-octafluorocyclopentene |
| FC-C151-10y | cyclo-$CF_2CF=CFCF_2CF_2CF_2-$ | 1,2,3,3,4,4,5,5,6,6-decafluorocyclohexene |

The compounds listed in Table 2 are available commercially or may be prepared by processes known in the art.

In addition to the inventive compounds described above, the bromine-containing fluorocarbons or hydrofluorocarbons presented in Table 3 can be used as aerosol propellants.

The compounds listed in Table 3 are available commercially or may be prepared by processes known in the art.

1-Bromo-3,3,4,4,4-pentafluoro-1-butene may be prepared by a three step sequence beginning with reaction of phosphorous tribromide with 3,3,4,4,4-pentafluoro-1-butanol to give

TABLE 3

| Structure | Chemical Names |
|---|---|
| $CF_2=CHCF_2Br$ | 3-bromo-1,1,3,3-tetrafluoropropene |
| $CF_2=CFCBrH_2$ | 3-bromo-1,1,2-trifluoropropene |
| $CHF=CBrCF_3$ | 2-bromo-1,3,3,3-tetrafluoropropene |
| $CHF=CHCBrF_2$ | 3-bromo-1,3,3-trifluoropropene |
| $CHF=CBrCHF_2$ | 2-bromo-1,3,3-trifluoropropene |
| $CHBr=CFCF_3$ | 1-bromo-2,3,3,3-tetrafluoropropene |
| $CHBr=CHCF_3$ | 1-bromo-3,3,3-trifluoropropene |
| $CH_2=CBrCF_3$ | 2-bromo-3,3,3-trifluoropropene |
| $CH_2=CFCBrF_2$ | 3-bromo-2,3,3-trifluoropropene |
| $CFBr=CHCF_3$ | 1-bromo-1,3,3,3-tetrafluoropropene |
| $CFBr=CFCF_3$ | 1-bromopentafluoropropene |
| $CH_2=CBrCF_2CF_3$ | 2-bromo-3,3,4,4,4-pentafluoro-1-butene |
| $CHBr=CHCF_2CF_3$ | 1-bromo-3,3,4,4,4-pentafluoro-1-butene |
| $CH_2=CHCF_2CF_2Br$ | 4-bromo-3,3,4,4-tetrafluoro-1-butene |
| $CH_2=CHCBrFCF_3$ | 3-bromo-3,4,4,4-tetrafluoro-1-butene |
| $CF_3CBr=CFCF_3$ | 2-bromo-1,1,1,3,4,4,4-heptafluoro-2-butene |
| $CH_3CBr=CHCF_3$ | 2-bromo-4,4,4-trifluoro-2-butene |
| $CF_3CBr=CHCH_3$ | 2-bromo-1,1,1-trifluoro-2-butene |
| $(CF_3)_2C=CHBr$ | 1-bromo-3,3,3-trifluoro-2-(trifluoromethyl)-propene |
| $CF_3CF=CBrCF_2CF_3$ | 3-bromo-1,1,1,2,4,4,5,5,5-nonafluoro-2-pentene |
| $E$-$CHF_2CBr=CFC_2F_5$ | E-2-bromo-1,1,3,4,4,5,5,5-octafluoro-2-pentene |
| $Z$-$CHF_2CBr=CFC_2F_5$ | Z-2-bromo-1,1,3,4,4,5,5,5-octafluoro-2-pentene |
| $CF_2=CBrCHFC_2F_5$ | 2-bromo-1,1,3,4,4,5,5,5-octafluoro-1-pentene |
| $CHBr=CF(CF_2)_2CHF_2$ | 1-bromo-2,3,3,4,4,5,5-heptafluoro-1-pentene |
| $CH_2=CBrCF_2C_2F_5$ | 2-bromo-3,3,4,4,5,5,5-heptafluoro-1-pentene |
| $CF_2=CHCF_2CH_2CBrF_2$ | 5-bromo-1,1,3,3,5,5-hexafluoro-1-pentene |
| $(CF_3)_2CFCBr=CH_2$ | 2-bromo-3,4,4,4-tetrafluoro-3-(trifluoromethyl)-1-butene |
| $CF_2=C(CH_2Br)CF_3$ | 2-(bromomethyl)-1,1,3,3,3-pentafluoropropene |
| $CH_2=C(CBrF_2)CF_3$ | 2-(bromodifluoromethyl)-3,3,3-trifluoropropene |
| $(CF_3)_2CHCH=CHBr$ | 1-bromo-4,4,4-trifluoro-3-(trifluoromethyl)-1-butene |
| $(CF_3)_2C=CHCH_2Br$ | 4-bromo-1,1,1-trifluoro-2-(trifluoromethyl)-2-butene |
| $CH_2=CHCF(CF_3)CBrF_2$ | 3-(bromodifluoromethyl)-3,4,4,4-tetrafluoro-1-butene |
| $CF_3CF_2CF_2CBr=CH_2$ | 2-bromo-3,3,4,4,5,5,5-heptafluoro-1-pentene |
| $CF_3(CF_2)_3CBr=CH_2$ | 2-bromo-3,3,4,4,5,5,6,6,6-nonafluoro-1-hexene |

4-bromo-1,1,1,2,2-pentafluorobutane. Thermal bromination of 4-bromo-1,1,1,2,2-pentafluorobutane at 350-400° C. gives 4,4-dibromo-1,1,1,2,2-pentafluorobutane which may in turn be heated with powdered potassium hydroxide to give the desired bromobutene.

2-Bromo-3,4,4,4-tetrafluoro-3-(trifluoromethyl)-1-butene may be prepared by addition of bromine to 3,4,4,4-tetrafluoro-3-(trifluoromethyl)-1-butene followed by treatment of the resulting dibromide with ethanolic potassium hydroxide.

Many of the compounds of Formulas I, Table 1, Table 2 and Table 3 exist as different configurational isomers or stereoisomers. When the specific isomer is not designated, the disclosure herein is intended to include all single configurational isomers, single stereoisomers, or any combination thereof. For instance, $CF_3CH=CHCF_3$ is meant to represent the E-isomer, Z-isomer, or any combination or mixture of both isomers in any ratio. Another example is $C_2F_5CF_2CH=CH-CF_2C_2F_5$, by which is represented the E-isomer, Z-isomer, or any combination or mixture of both isomers in any ratio.

Aerosol propellants may comprise a single compound as listed, for example, in Table 2, or may comprise a combination of compounds from Table 2 or, alternatively, a combination of compounds from Table 1, Table 2, Table 3, and/or Formula I.

The amount of the fluorocarbons (FCs) or HFCs contained in the present compositions (from, e.g., Formula I, Table 1, or Table 2, or Table 3) can vary widely, depending the particular application, and compositions containing more than trace amounts and less than 100% of the compound are within broad the scope of the present disclosure. Preferably, the compositions have a Global Warming Potential (GWP) of not greater than 150, more preferably not greater than 100, and even more preferably not greater than 75. As used herein, "GWP" is measured relative to that of carbon dioxide and over a 100-year time horizon, as defined in "The Scientific Assessment of Ozone Depletion, 2002, a report of the World Meteorological Association's Global Ozone Research and Monitoring Project," which is incorporated herein by reference.

The present compositions also preferably have an Ozone Depletion Potential (ODP) of not greater than 0.05, more preferably not greater than 0.02 and even more preferably about zero. As used herein, "ODP" is as defined in "The Scientific Assessment of Ozone Depletion, 2002, A report of the World Meteorological Association's Global Ozone Research and Monitoring Project," which is incorporated herein by reference.

The compositions may be prepared by any convenient method to combine the desired amounts of the individual components. A preferred method is to weigh the desired component amounts and thereafter combine the components in an appropriate vessel. Agitation may be used, if desired.

The propellants may comprise a single compound as listed, for example, in Table 1, or may comprise a combination of compounds of Formula I, Table 1, Table 2, and/or Table 3. Additionally, many of the compounds described herein may exist as different configurational isomers or stereoisomers. The disclosure herein is intended to include all single configurational isomers, single stereoisomers, or any combination thereof. For instance, F11E is meant to represent the E-isomer, Z-isomer, or any combination or mixture of both isomers in any ratio. Another example is F33E, by which is represented the E-isomer, Z-isomer, or any combination or mixture of both isomers in any ratio.

Preferably, the propellants disclosed herein have a Global Warming Potential (GWP) of not greater than 150, more preferably not greater than 100, and even more preferably not greater than 75. As used herein, "GWP" is measured relative to that of carbon dioxide and over a 100-year time horizon, as defined in "The Scientific Assessment of Ozone Depletion, 2002, a report of the World Meteorological Association's Global Ozone Research and Monitoring Project," which is incorporated herein by reference.

The present compositions also preferably have an Ozone Depletion Potential (ODP) of not greater than 0.05, more preferably not greater than 0.02 and even more preferably about zero. As used herein, "ODP" is as defined in "The Scientific Assessment of Ozone Depletion, 2002, A report of the World Meteorological Association's Global Ozone Research and Monitoring Project," which is incorporated herein by reference.

The compositions may be prepared by any convenient method to combine the desired amounts of the individual components. A preferred method is to weigh the desired component amounts and thereafter combine the components in an appropriate vessel. Agitation may be used, if desired.

The propellant composition comprises, more preferably consists essentially of, and, even more preferably, consists of compositions disclosed herein. The active ingredient to be sprayed together with inert ingredients, solvents, and other materials may also be present in the sprayable mixture. Preferably, the sprayable composition is an aerosol.

Another embodiment of the present disclosure provides a process for producing aerosol products comprising the step of adding a composition as disclosed herein to active ingredients in an aerosol container, wherein said composition functions as a propellant.

The compositions are capable of providing nonflammable, liquefied gas propellant and aerosols that do not contribute substantially to global warming. The present compositions can be used to formulate a variety of industrial aerosols or other sprayable compositions such as contact cleaners, dusters, lubricant sprays, mold release sprays, and the like, and consumer aerosols such as personal care products (such as, e.g., hair sprays, deodorants, and perfumes), household products (such as, e.g., waxes, polishes, pan sprays, room fresheners, and household insecticides), and automotive products (such as, e.g., cleaners and polishers), as well as medicinal materials such as anti-asthma and anti-halitosis medications. Examples of this includes metered dose inhalers (MDIs) for the treatment of asthma and other chronic obstructive pulmonary diseases and for delivery of medicaments to accessible mucous membranes or intranasally.

All such products utilize the pressure of a propellant gas or a mixture of propellant gases (i.e., a propellant gas system) to expel active ingredients from the container. For this purpose, most aerosols employ liquefied gases which vaporize and provide the pressure to propel the active ingredients when the valve on the aerosol container is pressed open.

The medicinal aerosol and/or propellant and/or sprayable compositions in many applications include, in addition to a compound disclosed herein, a medicament such as a beta-agonist, a corticosteroid or other medicament, and, optionally, other ingredients, such as surfactants, solvents, other propellants, flavorants, and other excipients. The compositions disclosed herein, unlike many compositions previously used in these applications, have good environmental properties and are not considered to be potential contributors to global warming. The present compositions therefore provide in certain preferred embodiments substantially nonflammable, liquefied gas propellants having very low GWPs.

All of the compositions and methods disclosed and claimed herein can be made and executed without undue experimentation in light of the present disclosure. While the compositions and methods disclosed herein have been described in terms of preferred embodiments, it will be apparent to those of skill in the art that variations may be applied to the compositions and methods and in the steps or in the sequence of steps of the method described herein without departing from the concept, spirit, and scope of the present disclosure. More specifically, it will be apparent that certain agents which are chemically related may be substituted for the agents described herein while the same or similar results would be achieved. All such similar substitutes and modifications apparent to those skilled in the art are deemed to be within the spirit, scope, and concept of the present disclosure as defined by the appended claims.

EXAMPLES

The present disclosure is further defined in the following Examples. It should be understood that these Examples, while indicating preferred embodiments, are given by way of illustration only. From the above discussion and these Examples, one skilled in the art can ascertain the preferred features, and without departing from the spirit and scope thereof, can make various changes and modifications to adapt it to various uses and conditions.

Example 1

55% VOC Hair Spray

A 55% VOC (volatile organic compound) hairspray was formulated as follows:

|  | Wt % |
| --- | --- |
| Octylacrylamide/acrylates/butylaminoethyl methylacrylate copolymer (National Starch Amphomer LV-71) | 5.0 |
| AMP (2-amino-2-methyl-1-propanol) | 1.0 |
| Water | 3.5 |
| Ethanol | 55.0 |
| Propellant | 35.0 |
| Vapor Pressure @ 70 F. | 40 psig |

The formulation was one phase indicating complete miscibility and showed good spray patterns and delivery.

Example 2

Air Freshener

An air freshener was formulated as follows:

|  | Wt % |
| --- | --- |
| Fragrance (Dragoco 0/716873 mixed flowers scent) | 1.0 |
| Water | 4.0 |
| Ethanol | 30.0 |
| Propellant | 65.0 |
| Vapor Pressure @ 70 F. | 48 psig |

The formulation was one phase indicating complete miscibility and showed good spray patterns and delivery.

Example 3

Fragrance

A fragrance was formulated as follows:

|  | Wt % |
| --- | --- |
| Perfume (Dragoco 0/716873 mixed flowers scent) | 3.0 |
| Water | 15.0 |
| Ethanol | 70.0 |
| Propellant | 12.0 |
| Vapor Pressure @ 70 F. | 17 psig |

The formulation was one phase indicating complete miscibility and showed good spray patterns and delivery.

Example 4

Aerosol Antiperspirant

An aerosol antiperspirant was formulated as follows:

|  | Wt % |
| --- | --- |
| Aluminum chlorohydrate (Reheis Activated ACH Modified R277-265A) | 10.0 |
| Isopropyl myristate | 6.0 |
| Silicone fluid DC-344 | 6.0 |
| Quaternium-18 hectorite (Rheox Bentone 38) | 0.5 |
| Ethanol | 2.0 |
| Propellant | 75.0 |
| Propellant | 12.0 |
| Vapor Pressure @ 70 F. | 48 psig |

The formulation provided good suspendability for the antiperspirant active, showed good spray patterns and delivery, and did not plug the valve.

Similar formulations can also be developed for household disinfectants, insect foggers, and spray paints using the compositions of the present disclosure.

We claim:

1. An aerosol dispensing system comprising a sealed container equipped with an aerosol dispensing valve and a propellant, wherein said propellant comprises at least one hydrofluoroolefin selected from the group consisting of: $CF_3CH=CHCF_3$, $CF_3CH=CHC_2F_5$, $CF_3CH=CHCF_2C_2F_5$, $CF_3CH=CHCF(CF_3)_2$, $C_2F_5CH=CHC_2F_5$, $CF_3CH=CH(CF_2)_3CF_3$, $CF_3CH=CHCF_2CF(CF_3)_2$, $CF_3CH=CHCF(CF_3)C_2F_5$, $CF_3CH=CHC(CF_3)_3$, $C_2F_5CH=CHCF_2C_2F_5$, and $C_2F_5CH=CHCF(CF_3)_2$.

2. The aerosol dispensing system of claim 1, wherein the propellant consists essentially of the hydrofluorocarbon.

3. The aerosol dispensing system of claim 1, wherein the propellant has a vapor pressure in a range of from about 138 to about 621 kPA at 21° C.

4. The aerosol dispensing system of claim 1, wherein the aerosol is a cleaner, duster, personal care product, automotive product, or medicament.

* * * * *